United States Patent [19]

Shirahata

[11] Patent Number: 5,312,949
[45] Date of Patent: May 17, 1994

[54] METHOD FOR THE PREPARATION OF TRIORGANOCHLOROSILANE

[75] Inventor: Akihiko Shirahata, Chiba, Japan

[73] Assignee: Dow Corning Toray Silicone Co., Ltd., Tokyo, Japan

[21] Appl. No.: 140,593

[22] Filed: Oct. 21, 1993

[30] Foreign Application Priority Data

Nov. 27, 1992 [JP] Japan .................. 4-341445

[51] Int. Cl.$^5$ .............. C07F 7/08; C07F 7/12
[52] U.S. Cl. .................................. 556/477
[58] Field of Search .......................... 556/477

[56] References Cited

U.S. PATENT DOCUMENTS

| | | | |
|---|---|---|---|
| 4,053,495 | 10/1977 | Deinhammer et al. | 556/477 |
| 4,665,209 | 5/1987 | Corriu et al. | 556/477 X |
| 5,258,535 | 11/1993 | Ishikawa et al. | 556/477 X |

Primary Examiner—Paul F. Shaver
Attorney, Agent, or Firm—William F. Boley

[57] ABSTRACT

A method for the preparation of triorganochlorosilane with the general formula $$R^1R^2R^3SiCl,$$

where $R^1$, $R^2$, and $R^3$ are independently selected from a group consisting of substituted and unsubstituted monovalent hydrocarbon groups, wherein said method is characterized by the reaction of hydrogen chloride with triorganohydrosilane with the general formula $$R^1R^2R^3SiH,$$

where $R^1$, $R^2$ and $R^3$ are as previously described, in the presence of a Group 8 transition metal or complex thereof.

5 Claims, No Drawings

METHOD FOR THE PREPARATION OF TRIORGANOCHLOROSILANE

BACKGROUND OF INVENTION

The present invention relates to a method for the preparation of triorganochlorosilane.

Triorganochlorosilane is used as an intermediate for silicone products such as silicone rubbers, silicone oils, and so forth. Triorganochlorosilane is also used as a silylating agent for the protection of functional groups on precursors during the synthesis of organic chemicals such as pharmaceuticals, agrichemicals, dyes, and so forth.

Methods for the preparation of triorganochlorosilane from triorganohydrosilane include the reaction of triorganohydrosilane with chlorine.

Specifically, triorganochlorosilane carrying a nonmethyl substituent on the silicon is generally synthesized by first reacting SiH-containing diorganochlorosilane with an organometallic compound (e.g., Grignard reagent, etc.) to yield the triorganohydrosilane and then reacting the triorganohydrosilane with chlorine to afford the triorganochlorosilane.

There has recently been recognition of the extreme usefulness of highly sterically hindered silylating agents with a better protective group inertness than trimethylchlorosilane, for example, trialkylchlorosilanes such as tert-butyldimethylchlorosilane, triisopropylchlorosilane, and triethylchlorosilane. As a result, such silylating agents are being used with increasing frequency. As explained above, silylating agents carrying such substitutents can be synthesized starting from a dialkylhydrochlorosilane. The necessary alkyl group is first introduced onto the silicon atom, and the Si-H group on the resulting trialkylhydrosilane is then chlorinated with chlorine. A drawback to this method is the inconvenience associated with the handling of chlorine, and sulfuryl chloride ($SO_2Cl_2$), a well-known chlorine equivalent, is therefore used in some cases in place of chlorine.

However, the chlorine and sulfuryl chloride (chlorine equivalent) used in this prior-art method exercise a poor reaction selectivity. This results in the synthesis of both trialkylchlorosilane (chlorination of the silicon-hydrogen bond) and chloroalkyl-containing silane by-products (chlorination of carbon-hydrogen bonds on the alkyl group), and the yield of the desired trialkylchlorosilane is therefore diminished. In addition, these chloroalkylsilane by-products do not currently have any value insofar as practical applications are concerned, and their disposal as industrial wastes is problematic from the standpoint of environmental preservation.

The present invention was developed as the result of extensive investigations by the inventor in order to solve the problem described above. The preparative method in accordance with the present invention makes possible the high-yield synthesis of triorganochlorosilane without the generation of by-products.

SUMMARY OF INVENTION

A method for the preparation of triorganochlorosilane with the general formula $$R^1R^2R^3SiCl,$$

where $R^1$, $R^2$, and $R^3$ are independently selected from a group consisting of substituted and unsubstituted monovalent hydrocarbon groups, wherein said method is characterized by the reaction of hydrogen chloride with triorganohydrosilane with the general formula $$R^1R^2R^3SiH,$$

where $R^1$, $R^2$ and $R^3$ are as previously described, in the presence of a Group 8 transition metal or complex thereof.

DESCRIPTION OF INVENTION

The present invention relates to a method for the preparation of triorganochlorosilane with the general formula $$R^1R^2R^3SiCl,$$

where $R^1$, $R^2$, and $R^3$ are independently selected from a group consisting of substituted and unsubstituted monovalent hydrocarbon groups, wherein said method is characterized by the reaction of hydrogen chloride with triorganohydrosilane with the general formula $$R^1R^2R^3SiH,$$

where $R^1$, $R^2$, and $R^3$ are as previously described, in the presence of a Group 8 transition metal or complex thereof.

To explain the preceding in greater detail, the $R^1$, $R^2$, and $R^3$ in the starting triorganohydrosilane used by the present invention represent one or more species of substituted or unsubstituted monovalent hydrocarbon groups. These groups are nonexhaustively exemplified by alkyl groups such as methyl, ethyl, propyl, and so forth; alkenyl groups such as vinyl, allyl, hexenyl, and so forth; cycloalkyl groups such as cyclohexyl, cycloheptyl, and so forth; aryl groups such as phenyl, tolyl, xylyl, and so forth; aralkyl groups such as benzyl, phenylethyl, and so forth; and halogen-substituted monovalent hydrocarbon groups such as trifluoropropyl, pentafluorobutyl, chloromethyl, chlorophenyl, and so forth. Among the preceding, the alkyl-containing triorganohydrosilanes, the trialkylsilanes, are considered optimal.

Said trialkylsilanes are exemplified by triethylsilane, tributylsilane, hexyldimethylsilane, cyclohexyldimethylsilane, diisopropylmethylsilane, tert-butyldimethylsilane, and triisopropylsilane. These organohydrosilanes can be synthesized by the action of an alkylmetal compound (e.g., Grignard reagent or alkyllithium) on a variety of organochlorosilanes.

The Group 8 transition metals and complexes thereof used in the instant invention are exemplified by ruthenium, rhodium, palladium, iridium, platinum, and their complexes. Among these, chloroplatinic acid and homogeneous platinum complexes such as the platinum/-divinyltetramethyldisiloxane complex are specifically preferred because they have high catalytic activities. The quantity of addition of these catalysts varies with the type of catalyst. Viewed from the perspective of the reaction rate and economics, homogeneous catalysts should be used at 1 ppm to 1,000 ppm and preferably at 10 ppm to 500 ppm in relation to the organohydrosilane, while heterogeneous catalysts should be used at 10 ppm to 10,000 ppm and preferably at 100 ppm to 5,000 ppm in relation to the organohydrosilane.

The general range for the reaction temperature (introduction of hydrogen chloride gas) is room temperature to 180° C., while the preferred range based on a consideration of the reaction rate is 50° C. to 180° C. This upper limit on the reaction temperature permits the reaction to be run under reflux in the case of trialkylsilanes with low to moderate boiling points. However, the use of excessively high temperatures with homogeneous catalysts can result in conversion into the elemental metal and precipitation from the reaction system with a resulting loss in activity.

This reaction is generally run without the use of solvent. When the reaction has been completed, the desired organochlorosilane can then be isolated by distillation of the reaction mixture without additional work-up. However, the reaction can be run in solvent as desired. Operable solvents for this purpose are exemplified by aromatic hydrocarbons such as toluene, xylene, chlorobenzene, and so forth; hydrocarbons such as hexane, cyclohexane, n-heptane, n-octane, and so forth; ethers; and halogenated hydrocarbons.

The invention will be explained in greater detail below through working examples, in which %=weight %. These examples are not intended to limit the scope of the present claims.

EXAMPLE 1

A thermometer, hydrogen chloride gas inlet tube, and reflux condenser were fitted to a stirrer-equipped 500 mL four-neck flask, and 270 g triisopropylsilane was then introduced into the flask. This was followed by the addition of 0.3 g 2% isopropanolic chloroplatinic acid hexahydrate solution and heating to 100° C. Hydrogen chloride gas was then introduced into the mixture. The evolution of very small hydrogen gas bubbles was observed. The introduction of hydrogen chloride gas was suspended after 8 hours. When the reaction mixture was analyzed by gas chromatography, only a peak for triisopropylchlorosilane was observed. The reaction mixture was subjected to vacuum distillation without additional work-up to yield 316 g triisopropylchlorosilane (purity≧99%, bp=64°-65° C./8 mmHg). The triisopropylchlorosilane yield was 96%.

EXAMPLE 2

A thermometer, hydrogen chloride gas inlet tube, and reflux condenser were fitted to a stirrer-equipped 300 mL four-neck flask, and 150 g tert-butyldimethylsilane was then introduced into the flask. This was followed by the addition of 0.2 g 2% isopropanolic chloroplatinic acid hexahydrate solution and heating to 95° C. Hydrogen chloride gas was then introduced into the mixture. The introduction of hydrogen chloride gas was suspended after 6 hours. Distillation at ambient pressure yielded 185 g tert-butyldimethylchlorosilane (purity≧99%, bp=126° C.). The tert-butyldimethylchlorosilane yield was 95%.

EXAMPLE 3

A thermometer, hydrogen chloride gas inlet tube, and reflux condenser were fitted to a stirrer-equipped 300 mL four-neck flask, and 150 g triethylchlorosilane was then introduced into the flask. This was followed by the addition of 0.2 g 2% isopropanolic chloroplatinic acid hexahydrate solution and heating to 100° C. Hydrogen chloride gas was then introduced into the mixture. The introduction of hydrogen chloride gas was suspended after 6 hours. Distillation at ambient pressure yielded 188 g triethylchlorosilane (purity≧99%, bp=144° C.). The tert-butyldimethylchlorosilane yield was 97%.

EXAMPLE 4

A thermometer, hydrogen chloride gas inlet tube, and reflux condenser were fitted to a stirrer-equipped 200 mL four-neck flask, and 80 g triisopropylsilane was then introduced into the flask. This was followed by the addition of 0.01 g platinum/divinyltetramethyldisiloxane complex and heating to 100° C. Hydrogen chloride gas was then introduced into the mixture. The introduction of hydrogen chloride gas was suspended after 4 hours. Vacuum distillation yielded 94 g triisopropylchlorosilane (purity≧99%). The triisopropylsilane yield was 97%.

EXAMPLE 5

A thermometer, hydrogen chloride gas inlet tube, and reflux condenser were fitted to a stirrer-equipped 200 mL four-neck flask, and 100 g methyldiisopropylsilane was then introduced into the flask. This was followed by the addition of 0.01 g platinum/divinyltetramethyldisiloxane complex and heating to 100° C. Hydrogen chloride gas was then introduced into the mixture. The introduction of hydrogen chloride gas was suspended after 4 hours. Distillation at ambient pressure yielded 122 g methyldiisopropylchlorosilane (purity≧99%, bp=146° C.). The methyldiisopropylchlorosilane yield was 97%.

We claim:

1. A method for preparation of triorganochlorosilane with the general formula $$R^1R^2R^3SiCl$$

where $R^1$, $R^2$, and $R^3$ are independently selected from a group consisting of substituted and unsubstituted monovalent hydrocarbon groups, wherein said method is characterized by the reaction of hydrogen chloride with triorganohydrosilane with the general formula $$R^1R^2R^3SiH,$$

where $R^1$, $R^2$, and $R^3$ are as previously described, in the presence of a Group 8 transition metal or complex thereof.

2. The method of claim 1 for the preparation of triorganochlorosilane in which the triorganohydrosilane is trialkylsilane.

3. The method of claim 1 for the preparation of triorganochlorosilane in which the Group 8 transition metal is platinum.

4. The method of claim 1 for the preparation of triorganochlorosilane in which the Group 8 transition metal complex is selected from a group consisting of platinum/divinyltetramethyldisiloxane complex and isopropanic chloroplatinic acid hexahydrate.

5. The method of claim 1 for the preparation of triorganochlorosilane in which the method is conducted at a temperature within a range of about 50° C. to 180° C.

* * * * *